US012594414B2

(12) United States Patent
Alqarni

(10) Patent No.: US 12,594,414 B2
(45) Date of Patent: Apr. 7, 2026

(54) HEART SUPPORT AND MASSAGE MACHINE

(71) Applicant: Imam Abdulrahman Bin Faisal University, Dammam (SA)

(72) Inventor: Abdulrahman Athwan S. Alqarni, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 253 days.

(21) Appl. No.: 18/583,019

(22) Filed: Feb. 21, 2024

(65) Prior Publication Data

US 2025/0262423 A1     Aug. 21, 2025

(51) Int. Cl.
*A61M 60/191* (2021.01)
*A61M 1/00* (2006.01)

(52) U.S. Cl.
CPC ............ *A61M 60/191* (2021.01); *A61M 1/70* (2021.05); *A61M 2205/02* (2013.01);
(Continued)

(58) Field of Classification Search
CPC .. A61M 60/191; A61M 1/70; A61M 2205/02; A61M 2205/054; A61M 2205/10; A61M 2205/3331; A61M 2205/3368; A61M 2205/3379; A61M 2205/36; A61M 2205/502; A61M 2205/8206; A61M 2209/088
See application file for complete search history.

(56) References Cited

U.S. PATENT DOCUMENTS 4,536,893 A     8/1985 Parravicini
6,238,334 B1 *  5/2001 Easterbrook, III  . A61M 60/468
                                          600/16

(Continued)

FOREIGN PATENT DOCUMENTS

WO     2021/018814 A1     2/2021

OTHER PUBLICATIONS

Letsou et al. ; The CorInnova Implantable Cardiac Assist System for Direct Cardiac Compression ; Rev. Cardiovasc. Med. 23(6) ; Jun. 9, 2022 ; 10 Pages.
(Continued)

*Primary Examiner* — Unsu Jung
*Assistant Examiner* — Laura Hodge
(74) *Attorney, Agent, or Firm* — Oblon, McClelland, Maier & Neustadt, L.L.P.

(57) ABSTRACT

A heart support apparatus includes a heart wrap having a shape configured to conform with a heart of a patient. The heart wrap includes four inflatable compartments, each inflatable compartment is configured to cover one of a pair of atriums and a pair of ventricles. The apparatus includes a negative charge pad configured to deliver an electrical stimulus to the heart and a positive charge pad configured to receive the electrical stimulus. The negative and the positive charge pads are connected to a power source through negative and positive lead cables, respectively. An external device with four piston pumps is used to circulate fluids to the inflatable compartments. A first suction tube and a second suction tube remove a first fluid and a second fluid, respectively, from the heart wrap. A controller with program instructions controls the piston pumps.

20 Claims, 10 Drawing Sheets

(52) U.S. Cl.
CPC ... *A61M 2205/054* (2013.01); *A61M 2205/10*
(2013.01); *A61M 2205/3331* (2013.01); *A61M*
*2205/3368* (2013.01); *A61M 2205/3379*
(2013.01); *A61M 2205/36* (2013.01); *A61M*
*2205/502* (2013.01); *A61M 2205/8206*
(2013.01); *A61M 2209/088* (2013.01)

(56) References Cited

U.S. PATENT DOCUMENTS

| | | |
|---|---|---|
| 6,846,296 B1 | 1/2005 | Milbocker et al. |
| 6,918,870 B1 | 7/2005 | Hunyor et al. |
| 8,942,828 B1 | 1/2015 | Schecter |
| 2007/0167670 A1 | 7/2007 | Coleman et al. |

OTHER PUBLICATIONS

Ventricular assist device (VAD) ; mayoclinic.org ; Sep. 15, 2018 ;
16 Pages.

* cited by examiner

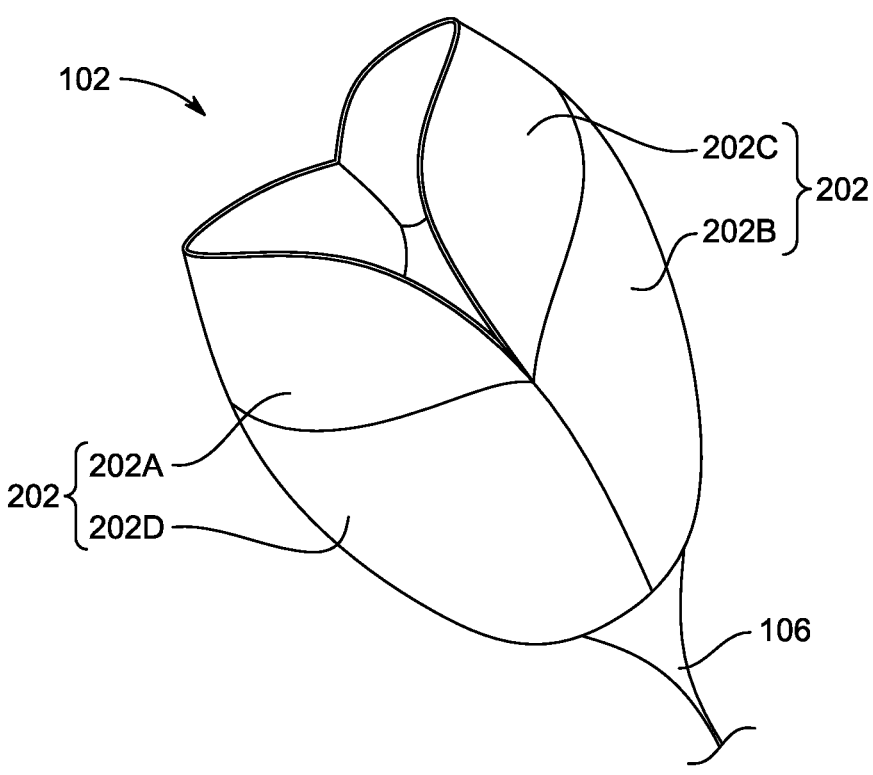
FIG. 2A
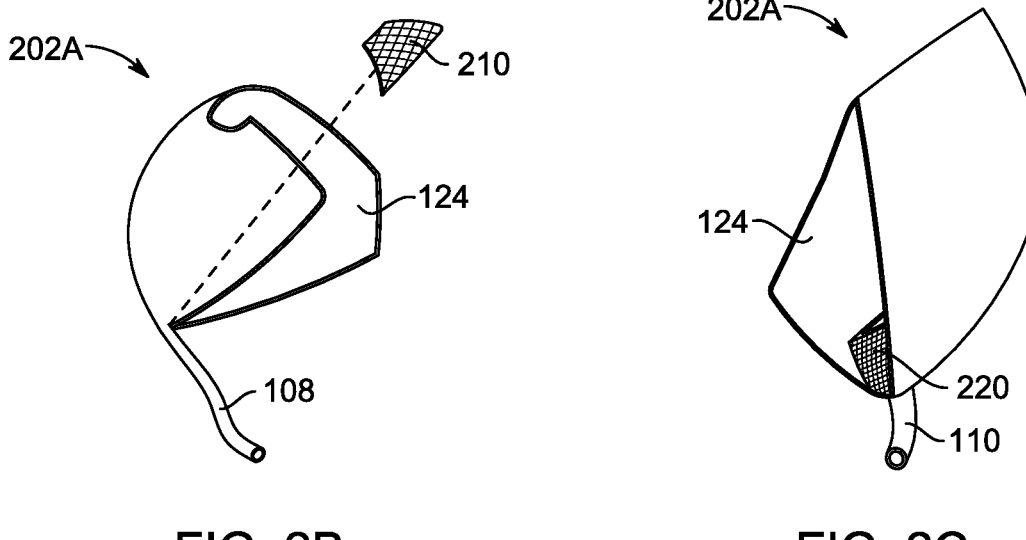
FIG. 2B          FIG. 2C

HEART SUPPORT AND MASSAGE MACHINE

BACKGROUND

Technical Field

The present disclosure relates to a minimally invasive surgical device for cardiac resuscitation. In particular, the present disclosure is directed to a heart support apparatus for massaging a heart of a patient to resuscitate the heart.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The heart is one of the most important organs in a human body. Due to stressful lifestyles, poor eating habits, injuries, illnesses, or genetic conditions, a number of people face multiple cardiac health issues. These issues, when left untreated at initial stages, transform into serious cardiac diseases such as, but are not limited to, coronary artery disease (CAD), arrhythmia, congestive heart failure (CHF), and myocardial infarction. The above specified diseases render the human heart weak and not apt for functioning at its full capacity thereby reducing the chance of survival of a patient in cases of heart malfunction. In some cases, surgical intervention is needed to restore the heart to full functioning capacity. Specifically, in recent times, open heart surgery has stood out as a promising approach to save countless lives as it allows a cardiac surgeon to perform necessary surgical procedures with relatively easy access to the heart. However, open heart surgery along with other surgical procedures performed on the human heart are complex procedures and may result in multiple post-surgery complications. In order to alleviate some of these complications, cardiac resuscitation may be required, and or a general support may be required for the heart post-surgery. Existing heart support devices include cardiac assist devices such as active devices which provide auxiliary pumping action to supplement or assist the blood pumping action of the natural heart, as well as passive devices which support the heart without augmenting the natural heart's pumping action. In particular, a few cardiac assist devices are designed for short-term use such as a few days while others are intended for long term application such as a few months or years. In many cases, it is also desirable that such cardiac assist devices be detachable.

WO2021018814A1 discloses a cardiac assist device for contracting a human or animal heart, comprising a first patch configured to be placed from the outside onto the heart, and a second patch configured to be placed from the outside onto the heart. The cardiac assist device further includes a mechanical adjustment mechanism for mechanically adjusting the positional relationship between the first patch and the second patch so as to contract the heart situated therebetween. However, no comprehensive support including temperature monitoring for the heart of a patient or drainage of fluid build-up, post surgery is described.

U.S. Pat. No. 6,846,296B1 discloses methods and apparatus for attaching cardiac devices onto a natural heart by employing arrays of gripping elements, such as hooks or barbs. The gripping elements are designed to penetrate and lodge themselves in the epicardial tissue in order to secure the device to at least a portion of the surface of the heart muscle. However, comprehensive cardiac support device that protects entire surface of the heart is described.

Accordingly, it is one object of the present disclosure to provide a comprehensive cardiac support device and system that covers a major or substantially the entire surface of the heart muscle. The present disclosure provides an inflatable heart support device for massaging a heart of a patient to provide cardiac compressions, to assess and drain any excess fluid build-up around the heart, and maintain a core temperature around the heart muscle with use of a heart wrap and an external pumping device.

SUMMARY

In an exemplary embodiment, a heart support apparatus for massaging a heart of a patient is disclosed. The heart support apparatus includes a heart wrap having a shape configured to conform with the heart of the patient. The heart wrap is divided in four inflatable compartments such that each inflatable compartment of the four inflatable compartments is configured to cover one of a right atrium, a left atrium, a right ventricle, or a left ventricle of the heart, respectively. The heart support apparatus further includes a negative charge pad placed inside a first inflatable compartment of the four inflatable compartments that covers the right atrium of the heart configured to deliver an electrical stimulus to the heart of the patient. The negative charge pad is connected to a power source through a negative lead cable. The heart support apparatus further includes a positive charge pad placed inside a second inflatable compartment of the four inflatable compartments that covers the left ventricle of the heart configured to receive the electrical stimulus. The positive charge pad is connected to the power source through a positive lead cable. Further, the heart support apparatus includes an external device with four piston pumps and a fluid chamber configured to circulate one or more fluids to the four inflatable compartments of the heart wrap through a fluid tube. The heart support apparatus further includes a first suction tube configured to remove a first fluid from an internal space between an outer surface of the heart and an inner surface of the heart wrap. The heart support apparatus further includes a second suction tube configured to remove a second fluid from an outer space between an outer surface of the heart wrap and a chest cavity of the patient. Furthermore, the heart support apparatus includes a connector tube configured to connect the external device to the heart wrap. The connector tube includes the negative lead cable, the positive lead cable, the fluid tube, the first suction tube, and the second suction tube. Additionally, the first suction tube and the second suction tube are connected to a vessel in the external device to receive the first fluid and the second fluid. Moreover, the heart support apparatus includes a controller with program instructions configured to control a set of parameters of the four piston pumps.

In some embodiments, the four piston pumps are integrated with a pair of peristaltic pumps.

In some embodiments, a first peristaltic pump of the pair of peristaltic pumps is connected to two inflatable compartments of the four inflatable compartments of the heart wrap that cover the right atrium and the right ventricle.

In some embodiments, a second peristaltic pump of the pair of peristaltic pumps is connected to two inflatable compartments of the four inflatable compartments of the heart wrap that cover the left atrium and the left ventricle.

In some embodiments, the fluid chamber of the external device is configured to heat the one or more fluids through a dry heating element connected to the fluid chamber.

In some embodiments, the fluid chamber of the external device has a temperature control system with a temperature sensor.

In some embodiments, the fluid chamber of the external device includes an upstream inlet to fill the fluid chamber with the one or more fluids and a downstream outlet to withdraw the one or more fluids from the fluid chamber.

In some embodiments, the heart support apparatus includes a support to hold the connector tube for insertion of the connector tube into the chest cavity of the patient.

In some embodiments, the four piston pumps are at a top end of the fluid chamber and four outlet valves at a lower end.

In some embodiments, the four outlet valves are connected to the fluid tube.

In some embodiments, an inner surface of the four inflatable compartments of the heart wrap is a porous foam.

In some embodiments, the heart wrap is made of a biocompatible material.

In some embodiments, the heart wrap is made of a material selected from a silicon polymer and a poly vinyl chloride (PVC).

In some embodiments, the power source connected to the positive charge pad and the negative charge pad is coupled to the external device.

In some embodiments, each of the four piston pumps is coupled to a check valve resulting in four check valves configured to block backflow of the one or more fluids from the four outlet valves.

In some embodiments, the external device includes a pressure relief valve configured to control an amount of the one or more fluids pumped into the heart wrap.

In some embodiments, the external device includes a reservoir to receive excessive amount of the one or more fluids from the pressure relief valve.

In some embodiments, the external device is coupled to a plurality of pressure sensors and a plurality of flow sensors.

In some embodiments, the heart wrap has a cone shape.

In some embodiments, the controller is an electronic controller with a user-interface.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 2A is a schematic perspective view of the heart wrap of FIG. 1A, according to certain embodiments;

FIG. 2B is a schematic perspective view of an inflatable compartment of the heart wrap of FIG. 2A, according to certain embodiments;

FIG. 2C is a schematic perspective view of another inflatable compartment of the heart wrap of FIG. 2A, according to certain embodiments;

DETAILED DESCRIPTION

Figure 1A:
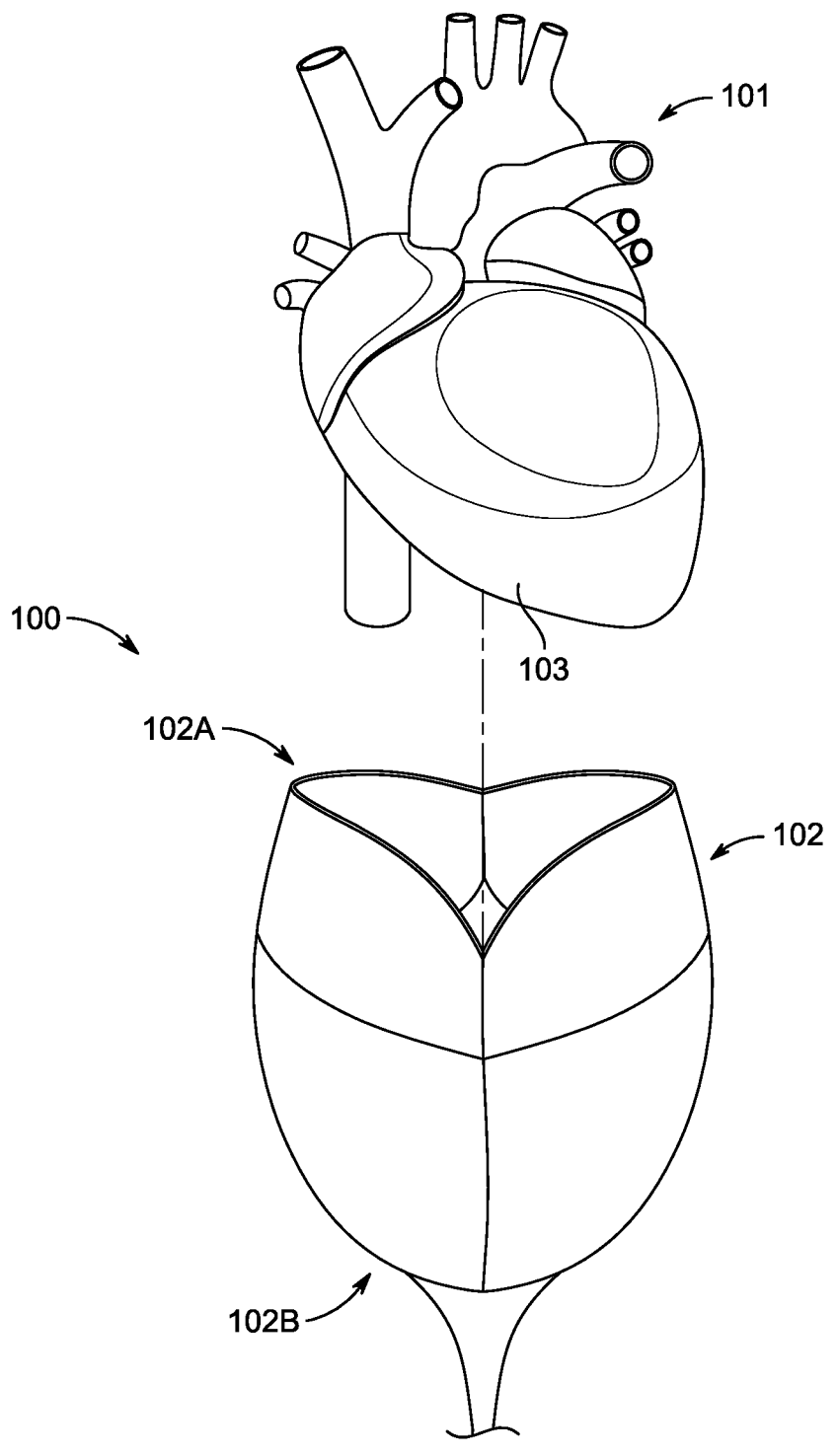
FIG. 1A is a schematic perspective diagram of a heart wrap of a heart support apparatus configured to attach with a heart of a patient, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about" and similar terms generally refer to ranges that include the identified value within a margin of 20%, 10%, or preferably 5%, and any values therebetween.

Aspects of the present disclosure are directed towards a heart support apparatus and system for massaging a heart of a patient. The heart support apparatus is configured to be used as a cardiac assist device for patients who have undergone one or more cardiac surgical procedures and may require external aid for proper functioning of a surgically repaired heart. The heart support apparatus, as described in the present disclosure, includes a heart wrap connected to an external device that includes a pumping unit, a fluid chamber, and temperature control, and a controller to control and monitor the heart support apparatus. The heart wrap of the support device is preferably formed of flexible biocompatible materials in order to be compatible with the heart of the patient.

Referring to FIG. 1A, a schematic perspective diagram of a heart support apparatus 100 configured to cover the muscle tissue of a heart 101 of a patient is illustrated, according to certain embodiments. In particular, a heart wrap 102 of the heart support apparatus 100 is shown in FIG. 1A. The heart support apparatus 100 is configured to massage the heart 101 of the patient. The heart wrap 102 is configured to wrap around an outer surface 103 of the heart 101. The heart wrap 102 has a shape configured to confirm with the heart 101 of the patient. In particular, the constructional features and dimensional specifications of the heart wrap 102 are configured to conform with a shape, a size, and overall dimensions of the heart 101 of the patient. In other words, the heart wrap 102 is configured to wrap around the heart 101 of the patient in order to provide external stimulus and support, as required by the patient. The external stimulus and support may include, but are not limited to, a heart massage, e.g., rhythmic or constant applications of force or pressure, chest compressions, electrical shock to resuscitate the heart 101, normothermia, and suction fluid around the outer surface of the heart 101. In an embodiment, the heart wrap 102 has a cone shape having a top end 102A opened to receive the heart 101 therethrough and a bottom end 102B closed and configured to attach with other accessory elements of the heart support apparatus 100 such as a pump. In other words, a circumferential length. i.e., a diameter of the bottom end 102B of the heart wrap, is smaller than a circumferential length, i.e., diameter of the top end 102A of the heart wrap 102, providing the heart wrap 102 the cone shape. Preferably, an upper opening of the heart wrap has a circular cross section that is deformable when installed in a patient. As shown in FIG. 1A, as aspect view of the device shows that the heart wrap is similar to a flower petal structure in which two ovoid sections overlap and/or nest to form a cup shape defined by two symmetrically extending portions and corresponding indents at the points where the ovoid shape begin to overlap. In some embodiments, the heart wrap 102 is formed of a biocompatible material. In some embodiments, the heart wrap 102 is made of a material selected from a silicon polymer and a polyvinyl chloride (PVC). The biocompatible material is an important part of the construction of the heart wrap 102 as it avoids cross-reaction between the heart wrap 102 and the heart 101 of the patient. In some embodiments, allergies of the patient are taken into consideration before selecting a particular material for the heart wrap 102.

Figure 1B:
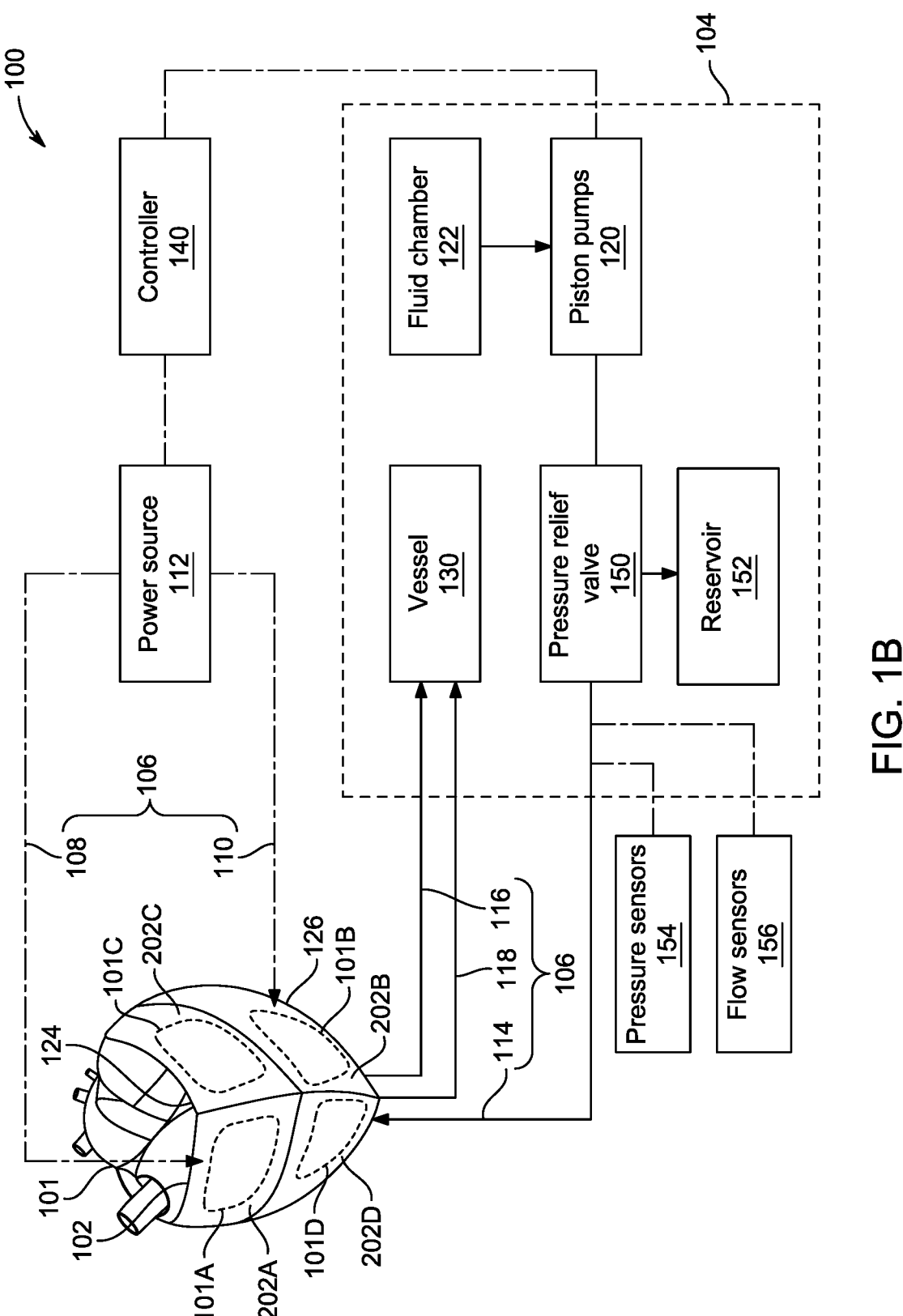
FIG. 1B is a schematic block diagram of the heart support apparatus, according to certain embodiments.

Referring to FIG. 1B, a schematic block diagram of the heart support apparatus 100 is illustrated, according to an embodiment of the present disclosure. The heart support apparatus 100 includes an external device 104 configured to communicate electrically and fluidly with the heart wrap 102. The external device 104 is a comprehensive machine including a plurality of operating elements configured to couple with the heart wrap 102 electrically and fluidly. In an embodiment, the external device 104 is configured to couple to the heart wrap 102 electrically and fluidly through a connector tube 106. The connector tube 106 includes a negative lead cable 108 and a positive lead cable 110 configured to electrically couple the external device 104 with the heart wrap 102. The negative lead cable 108 and the positive lead cable 110 are further connected to a power source 112 to derive an electric power therefrom to electrically actuate the heart wrap 102 for massaging the heart 101 of the patient.

Usually, a pacemaker is inserted in patients with heart failure, i.e., when heart does not pump blood in a regular manner. However, pacemakers give low energy to the heart and sometimes fail to overcome arrhythmias of the heart. The negative lead cable 108 and the positive lead cable 110 in addition to other components of the heart wrap 102 (as described later) facilitate to deliver shocks to resuscitate the heart when necessary. Further, the connector tube 106 includes a fluid tube 114, a first suction tube 116, and a second suction tube 118 configured to fluidly connect the external device 104 with the heart wrap 102. As such, the connector tube 106 is configured to operatively connect the external device 104 to the heart wrap 102 to massage the heart 101 of the patient.

Referring to FIGS. 1A and 1B, the external device 104 includes a plurality of piston pumps 120 and a fluid chamber 122 configured to circulate one or more fluids to the heart wrap 102 through the fluid tube 114. The one or more fluids are circulated around a heart process such as, normothermia and inflating the heart wrap 102. Inflating the heart wrap 102 allows the heart wrap 102 to push the heart muscles, atrium, or ventricular heart muscles, to circulate blood. Normothermia is defined as a body's core temperature of 36° C. After certain open-heart procedures, heart of a patient needs to be maintained at body's core temperature, this can help to regulate the temperature of other organs of the patient's body. In order to maintain the heart at a core temperature, one or more fluids from the fluid chamber 122 at a defined temperature at pumped using the plurality of piston pumps 120 from the external device 104 and circulated around the heart and within the heart wrap 102. The one or more fluids may include, but are not limited to, sterile water, and saline. Sterile water is widely available and is non-toxic, making it a safe choice for use. Further, sterile water has well-understood fluid dynamics properties, and the relatively low viscosity of sterile water allows for efficient circulation through the external device 104. In addition, sterile water has a high specific heat capacity, and it may absorb and release heat effectively. This property makes it suitable for temperature regulation within the heart wrap 102. Additionally, sterile water is chemically inert and does not react with most materials commonly used in medical equipment.

Furthermore, the first suction tube 116 and the second suction tube 118 are configured to remove a first fluid and a second fluid, respectively, from the heart wrap 102. In certain unforeseen situations, fluid gets accumulated in the pericardium, a sac that holds a heart. When accumulation of fluid happens quickly or involves a large amount of fluid, the excess fluid can take up too much space in the pericardium, compressing the heart and causing a life-threatening condition known as cardiac tamponade. The excess fluid is removed through a process of suctioning. In the present disclosure, removal of the first fluid relates to suctioning fluid from an internal space defined between the outer surface 103 of the heart 101 and an inner surface 124 of the heart wrap 102. Removal of the second fluid relates to suctioning fluid from an outer space defined between an outer surface 126 of the heart wrap 102 and a chest cavity (not shown) of the patient. If the first suction tube 116 vacuums up a greater quantity of fluid than the second suction tube 118, it may relate to a bleeding of the heart, helping a cardiologist plan for a solution. If the second suction tube 118 produces more fluid than the first suction tube 116, this might indicate accumulation of fluid in the pericardium or a bleed from a tissue surrounding the heart. The first suction tube 116 and the second suction tube 118 are further fluidly connected to a vessel 130 of the external device 104 to receive the first fluid and the second fluid. The vessel 130 may be a storage device configured to receive and store the first fluid and the second fluid. In other words, the first suction tube 116 and the second suction tube 118 are connected to the vessel 130 in the external device 104 to receive the first fluid and the second fluid, respectively. The contents of the vessel 130 may later be disposed of in a safe and controlled manner. Further, standard operating procedures may be set up for disposing and collecting bio fluids and the vessel 130 may be designed to comply with the industrial standards. The heart support apparatus 100 further includes a controller 140 with program instructions configured to control a set of parameters of the piston pumps 120. The controller 140 may be further communicated with the power source 112. In an embodiment, the controller 140 is an electronic controller with a user-interface. The user-interface allows a user to input data to the controller 140 for effectively operating the heart support apparatus 100. Furthermore, the heart support apparatus 100 includes a pressure relief valve 150 configured to control and maintain a pressure of the one or more fluids flowing through the fluid tube 114 at a desired pressure. A reservoir 152 is fluidly communicated with the pressure relief valve 150 to receive excess amounts of the fluids from the pressure relief valve 150. A plurality of pressure sensors 154 and a plurality of flow sensors 156 are fluidly coupled with the fluid tube 114 to detect a pressure and a flow rate, respectively, of the fluids flowing through the fluid tube 114. In some embodiments, the pressure relief valve 150, the plurality of pressure sensors 154, and the plurality of flow sensors 156 may be in electric communication with the controller 140 to control and maintain the desired pressure and desired flow rate of the fluids in the fluid tube 114.

Referring to FIG. 2A, a schematic perspective view of the heart wrap 102 is illustrated, according to certain embodiments. The heart wrap 102 is divided into a plurality of inflatable compartments 202. According to the present disclosure, the heart wrap 102 is divided into four inflatable compartments 202. The four inflatable compartments 202 include a first inflatable compartment 202A, a second inflatable compartment 202B, a third inflatable compartment 202C, and a fourth inflatable compartment 202D. Referring to FIG. 1B and FIG. 2A, the first inflatable compartment 202A is configured to cover a right atrium 101A of the heart 101, the second inflatable compartment 202B is configured to cover a left ventricle 101B of the heart 101, the third inflatable compartment 202C is configured to cover a left atrium 101C of the heart 101, and the fourth inflatable compartment 202D is configured to cover a right ventricle 101D of the heart 101. Hereafter, the four inflatable compartments, 202A, 202B, 202C, and 202D are commonly referred together as four inflatable compartments 202. In other words, each inflatable compartment of the four inflatable compartments 202 is configured to at least partially cover one of the right atrium 101A, the left atrium 101C, the right ventricle 101D, and the left ventricle 101B of the heart 101. As described earlier, the heart wrap 102 with the four inflatable compartments 202 is preferably of a cone shape with a wider circumference opening at a top end of the heart wrap 102 and a smaller circumference opening at a bottom end (e.g., in the form of a bi-truncate cone or ovoid with truncates at both top and bottom ends). In some embodiments, an inner surface of the four inflatable compartments 202 of the heart wrap 102 is a porous foam. The inner surface of the four inflatable compartments 202 corresponds to the inner surface 124 of the heart wrap 102. The porous foam is made of a medical grade biocompatible material. Also, the porous foam may be an open cell structure foam preferably catalyst-free polyurethane, more preferably an inner open cell structure with an outer impermeable thin skin. In a preferably embodiment that porous foam and corresponding outer skin consist of the same polyurethane or polysilicone polymer. The open cell structure of the porous foam may make it a suitable material for the inner surface of the four inflatable compartments 202 as well as sufficiently pliable and flexible to accommodate prolonged expansion and contraction cycles when in use in a patient, as the porosity may be altered as per requirements of the patient. Further, the connector tube 106 is configured to be connected at the bottom end 102B of the heart wrap 102.

Referring to FIG. 2B, a schematic perspective view of a portion of the heart wrap 102 is illustrated, according to certain embodiments. In particular, a perspective view of the first inflatable compartment 202A of the heart wrap 102 is schematically shown in FIG. 2B. The heart support apparatus 100 includes a negative charge pad 210 configured to be positioned near a sinoatrial node of the heart 101 of the patient. In some embodiments, the negative charge pad 210 is configured to be placed inside the first inflatable compartment 202A of the four inflatable compartments 202. The negative charge pad 210 detached from the first inflatable compartment 202A is shown in FIG. 2B. The negative charge pad 210 is configured to couple with the first inflatable compartment 202A covering the right atrium 101A of the heart 101. The negative charge pad 210 is configured to deliver an electrical stimulus to the heart 101 of the patient. In general, electrical stimulus is delivered to an unhealthy heart to perform cardioversion, in which an arrhythmia is converted into normal heartbeat through the above-mentioned electrical stimulus. The electrical stimulus may be either monophasic or biphasic. Monophasic stimuli include a single pulse of electricity, while biphasic stimulus includes delivery of two pulses of electricity in quick succession. The negative charge pad 210 is further connected to the power source 112 in order to harness the capability to deliver the electrical stimulus through the negative lead cable 108. The negative lead cable 108 further ensures the connection of the negative charge pad 210 to the external device 104. Preferably the negative charge pad is embedded into the polymer or polymer skin when the polymer is molded to form the inflatable compartment. For example, the major portion of the negative charge pad is embedded and thus covered with the foamed polymer and or polymer skin. Only a minor portion (e.g., less than 50% of the total surface area of the negative charge pad) is exposed outside the foamed polymer. Forming the heart wrap compartment in this manner permits careful design and charge pad heart tissue contact.

Referring to FIG. 2C, a schematic perspective view of a portion of the heart wrap 102 is illustrated, according to certain embodiments. In particular, a perspective view of the second inflatable compartment 202B of the heart wrap 102 is schematically shown in FIG. 2B. The heart support apparatus 100 includes a positive charge pad 220. The bottom portions of the respective inflatable compartment may nest at least partially within one another. In some embodiments, the positive charge pad 220 is configured to be placed inside the second inflatable compartment 202B of the four inflatable compartments 202. In particular, the positive charge pad 220 is configured to couple with the second inflatable compartment 202B covering the left ventricle 101B of the heart 101. The positive charge pad 220 is configured to receive the electrical stimulus as transmitted by the negative charge pad 210. The electrical stimulus transmits from the negative charge pad 210 to the positive charge pad 220, as a result, an assistance is provided to the heart 101 of the patient in case of an irregular heartbeat. The positive charge pad 220 is connected to the power source 112 through the positive lead cable 110. The positive lead cable 110 further ensures the connection of the positive charge pad 220 to the external device 104. In some embodiments, the power source 112 connected to the positive charge pad 220 and the negative charge pad 210 is coupled to the external device 104. As such, the power source 112 is configured to power the external device 104, which in turn supplies regulated power to the negative charge pad 210 and the positive charge pad 220. The power source 112 may refer to a, but is not limited to, direct current source, alternating current source, and a plurality of energy storage devices such as batteries.

Figure 3:
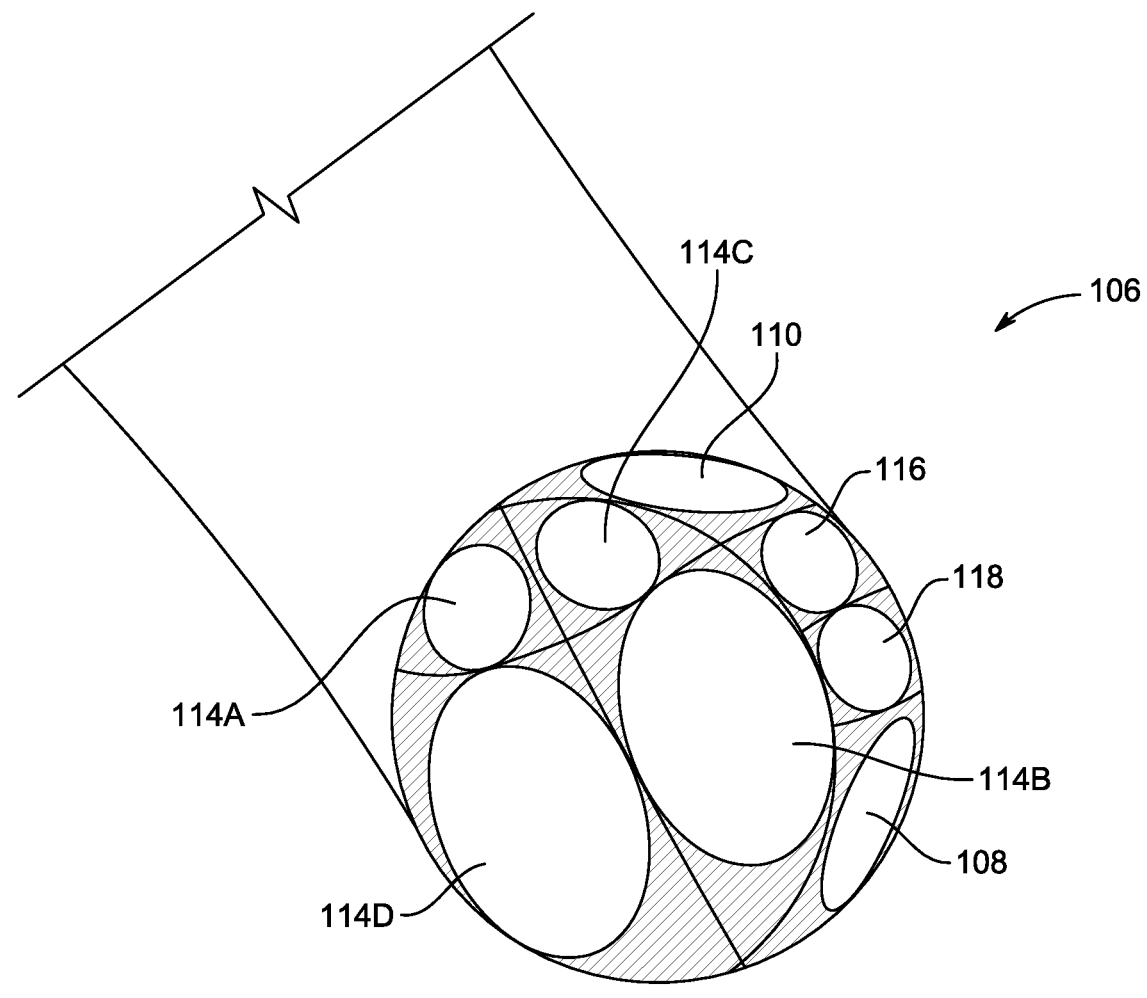
FIG. 3 is a schematic cross-sectional view of a connector tube of the heart support apparatus, according to certain embodiments.

Referring to FIG. 3, a schematic cross-sectional diagram depicting various tubes and cables of the connector tube 106 is illustrated, according to certain embodiments. The connector tube 106 is configured to connect the heart wrap 102 with the external device 104 of the heart support apparatus 100. In other words, the connector tube 106 is a main tube housing a plurality of tubes and cables to functionally couple the heart wrap 102 with the external device 104. Referring to FIG. 1B and FIG. 3, the connector tube 106 includes the negative lead cable 108, the positive lead cable 110, the fluid tube 114, the first suction tube 116, and the second suction tube 118. Each of multiple passages defined within the connector tube 106 is designated by the reference numbers corresponding to the negative lead cable 108, the positive lead cable 110, the first suction tube 116, and the second suction tube 118 for the sake of brevity in explanation. In an embodiment, the fluid tube 114 is connected to a right atrium passage 114A, a left atrium passage 114C, a right ventricle passage 114D, and a left ventricle passage 114B. In some embodiments, the connector tube 106 may house one or more extra components, such as, but not limited to, wires, sensor wires, and other electrical or fluid lines. In some embodiments, each of the right atrium passage 114A and the left atrium passage 114C may have a cross-sectional area in a range of about 7.5%-12.5% of a total cross-sectional area of the connector tube 106 and each of the right ventricle passage 114D and the left ventricle passage 114B may have a cross-sectional area of about 15%-20% of the total cross-sectional area of the connector tube 106. Also, each of the passages of the first and the second suction tubes 116, 118 may have a cross-sectional area of about 7.5%-10% of the total cross-sectional area of the connector tube 106. Similarly, each of the passages of the negative and the positive lead cables 108, 110 may have a cross-sectional area of about 7.5%-10% of the total cross-sectional area of the connector tube 106. In some embodiment, collective cross-sectional area of the negative and the positive lead cables 108, 110 may be less than 20%.

The first suction tube 116 is configured to remove the first fluid from the internal space between the outer surface 103 of the heart 101 and the inner surface 124 of the heart wrap 102. In other words, the heart support apparatus 100 includes the first suction tube 116 having one end coupled to the heart wrap 102 and another end coupled to the external device 104 in order to eliminate the first fluid, which may be formed between the inner surface 124 of the heart wrap 102 and the outer surface 103 of the heart 101 of the patient, to prevent any infection and maintain appropriate contact between the heart wrap 102 and the heart 101 of the patient. In some embodiments, the first fluid may include, but is not limited to, blood, platelets, plasma, and any other infectious fluid.

The second suction tube 118 is configured to remove the second fluid from the outer space between the outer surface 126 of the heart wrap 102 and the chest cavity of the patient. In some embodiments, one end of the second suction tube 118 may be placed inside the chest cavity and another end of the second suction tube 118 may be fluidly coupled with the external device 104. In particular, the heart support apparatus 100 may have a provision for the second suction tube 118 to be placed in the chest cavity of the patient in order to collect, via vacuum, the second fluid that may develop in the chest cavity when the patient is under treatment. In general, during open heart surgical procedures, blood and other fluids may pool in the chest cavity of the patient, making it difficult for a healthcare professional to clearly see the area of where the surgical procedure is being performed, this may increase chances of surgical complication. The second suction tube 118 is an integral component to alleviate the aforementioned issue.

Figure 4A:
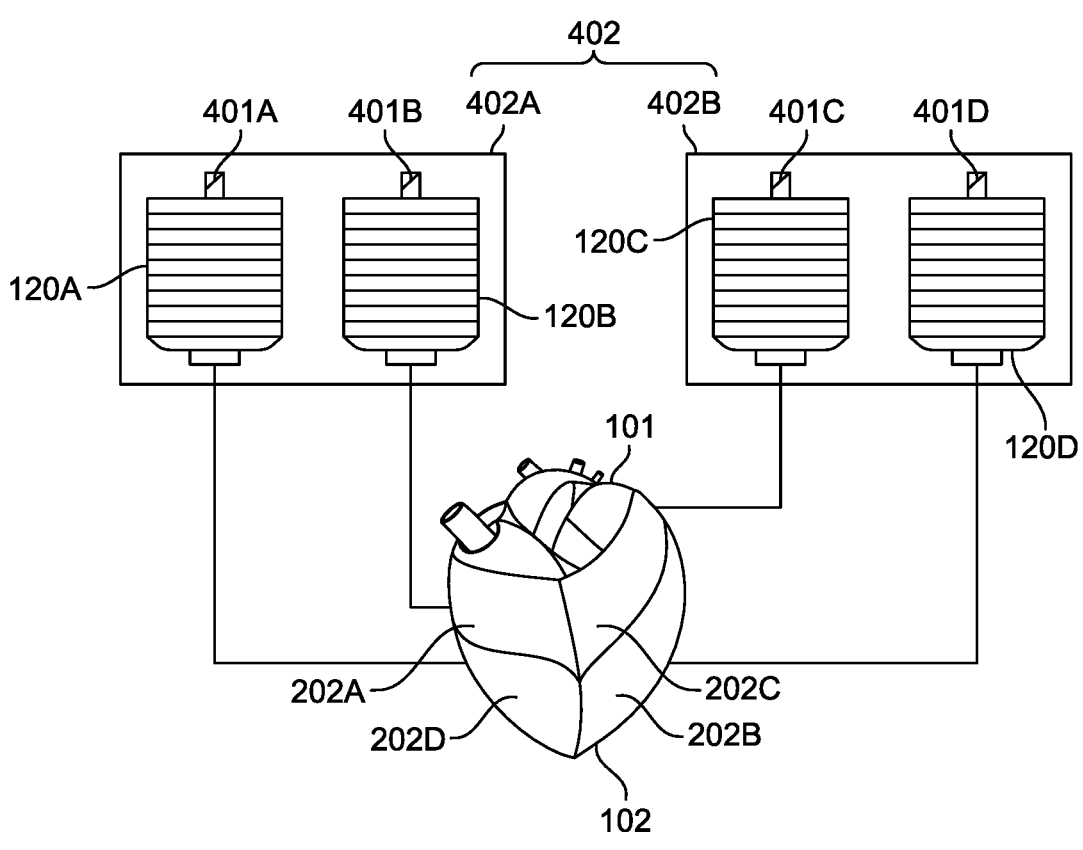
FIG. 4A is a schematic block diagram showing a plurality of piston pumps connecting to the heart wrap of FIG. 1B, according to certain embodiments.

Referring to FIG. 4A, a schematic block diagram of the plurality of piston pumps 120 connecting to the heart wrap 102 is illustrated, according to certain embodiments. Referring to FIG. 1B and FIG. 4A, the external device 104 includes a first piston pump 120A, a second piston pump 120B, a third piston pump 120C, and a fourth piston pump 120D. Hereafter, the first piston pump 120A, the second piston pump 120B, the third piston pump 120C, and the fourth piston pump 120D may be collectively referred as four piston pumps 120, as the each of the four piston pumps are structurally and functionally the same. The external device 104 further incudes the fluid chamber 122. As described before, the fluid chamber 122 is configured to circulate the one or more fluids to the four inflatable compartments 202 of the heart wrap 102 through the fluid tube 114. Piston pumps may be used to pump liquids and to compress gases. Piston pumps may be operated to deliver a wide pressure range, for example, from 5 to up to 100 psi. Pressure applied to a heart is calculated based on parameters such as, mass of the patient, and blood pressure requirement of a heart. In an embodiment, the four piston pumps 120A, 120B, 120C and 120D are coupled to a check valve 401A, 401B, 401C and 401D, respectively. The first check valve 401A, the second check valve 401B, the third check valve 401C, and the fourth check valve 401D are collectively referred as four check valves 401. As such, each of the four piston pumps 120 is fluidly coupled with each of the four check valves 401. In general, a check valve is a one-way valve that prevents backflow of a fluid. In the present disclosure, fluid flows from the fluid chamber 122 to the heart wrap 102 with the help of constant pressure generated by the four piston pumps 120, the check valve prevents loss of the constant pressure generation by the four piston pumps 120.

Further, the four piston pumps 120 are integrated with a pair of peristaltic pumps 402. In other words, the pair of peristaltic pumps 402 are configured to fluidly couple with the four piston pumps 120. Furthermore, maintaining sterility within the heart support apparatus 100 while using the four piston pumps 120 is paramount to ensure patient safety and prevent contamination. In order to achieve that, a closed system may be implied. The closed system refers to preventing the pistons of the four piston pumps 120 from coming in direct contact with the one or more fluids being pumped by the four piston pumps 120.

The pair of peristaltic pumps 402 include a first peristaltic pump 402A and a second peristaltic pump 402B. In general, a peristaltic pump or a roller pump is a type of positive displacement pump used for pumping a variety of fluids. The fluid is contained in a flexible tube fitted inside a circular pump casing. Traditional peristaltic pumps work through rotary motion. In an embodiment of the present disclosure, the first peristaltic pump 402A of the pair of peristaltic pumps 402 is connected to the two inflatable compartments 202A, 202D of the four inflatable compartments 202 of the heart wrap 102 that cover the right atrium 101A and the right ventricle 101D. In other words, the first peristaltic pump 402A is configured to fluidly couple with the first and the fourth inflatable compartments 202A, 202D in order to pump the one or more fluids to the right atrium 101A and the right ventricle 101D. The second peristaltic pump 402B of the pair of peristaltic pumps 402 is connected to the two inflatable compartments 202C, 202B of the four inflatable compartments 202 of the heart wrap 102 that cover the left atrium 101C and the left ventricle 101B. In other words, the second peristaltic pump 402B is configured to fluidly couple with the third and the second inflatable compartments 202C, 202B in order to pump the one or more fluids to the left atrium 101C and the left ventricle 101B. In some embodiments, the first peristaltic pump 402A may be fluidly coupled with the third and the second inflatable compartments 202C, 202B, and the second peristaltic pump 402B may be fluidly coupled with the first and the fourth inflatable compartments 202A, 202D.

In a healthy heart, a simultaneous occurrence of complete atrial contraction (facilitating ventricular filling) and relaxation (allowing for atrial refilling) is a crucial aspect of optimal cardiac function. The contraction and relaxation of both atria happen spontaneously at the same time. Subsequently, the ventricles undergo complete contraction, similarly occurring simultaneously in both ventricles, expelling blood into the pulmonary artery from the right ventricle and into the aorta from the left ventricle. In an example embodiment of the present disclosure, the first peristaltic pump 402A of the pair of peristaltic pumps 402 is connected to the two inflatable compartments in the atria 202A, 202C (right and left atria in one peristaltic pump) of the four inflatable compartments 202 of the heart wrap 102 that cover the right atrium 101A and the left atrium 101C to mitigate any potential fluid stagnation. In other words, the first peristaltic pump 402A is configured to fluidly couple with the first and the third inflatable compartments 202A, 202C in order to pump the one or more fluids to the right atrium 101A and the left atrium 101C. The second peristaltic pump 402B of the pair of peristaltic pumps 402 is connected to the two inflatable compartments 202D, 202B of the four inflatable compartments 202 of the heart wrap 102 that cover the right ventricle 101D and the left ventricle 101B to mitigate any potential fluid stagnation. In other words, the second peristaltic pump 402B is configured to fluidly couple with the fourth and the second inflatable compartments 202D, 202B in order to pump the one or more fluids to the right ventricle 101D and the left ventricle 101B. In some embodiments, the first peristaltic pump 402A may be fluidly coupled with the fourth and the second inflatable compartments 202D, 202B, and the second peristaltic pump 402B may be fluidly coupled with the first and the third inflatable compartments 202A, 202C.

Figure 4B:
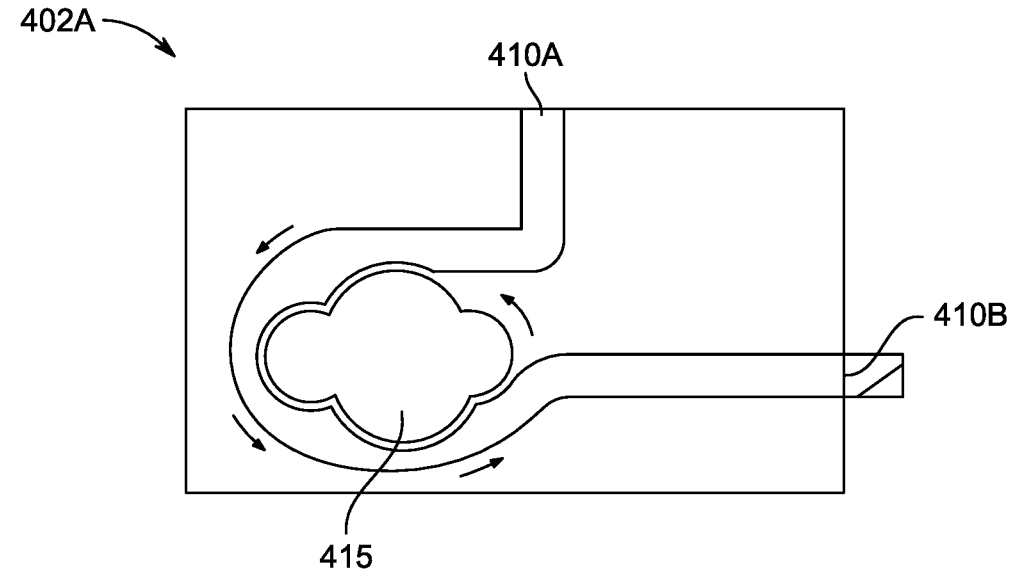
FIG. 4B is a schematic diagram of a peristaltic pump, in accordance with certain embodiments.

Referring to FIG. 4B, a schematic diagram of the first peristaltic pump 402A of the pair of peristaltic pumps 402 is illustrated, according to certain embodiments. The first and the second peristaltic pumps 402A, 402B have similar constructional details and dimensional specifications. Therefore, the first peristaltic pump 402A is explained in detail in order to maintain brevity in explanation. As can be seen from FIG. 4B, the first peristaltic pump 402A includes an inlet 410A and an outlet 410B. The inlet 410A is configured to receive the one or more fluids therein and the outlet 410B is configured to pump out the one or more fluids therefrom. The first peristaltic pump 402A further includes a rotary core 415. The rotary core 415 is responsible for generating rotary motion in the first peristaltic pump 402A in order to create the pumping force to pump the one or more fluids included in the heart support apparatus 100. In some embodiments, the first peristaltic pump 402A mimics a natural flow pattern of the heart 101 and helps prevent stagnation of the one or more fluids in the heart 101. The first peristaltic pump 402A creates negative pressure in order to withdraw the fluid present in the heart wrap 102. As such, the pair of peristaltic pumps 402 are responsible for generating negative pressure in contrast to the positive pressure generated by the four piston pumps 120.

Figure 5:
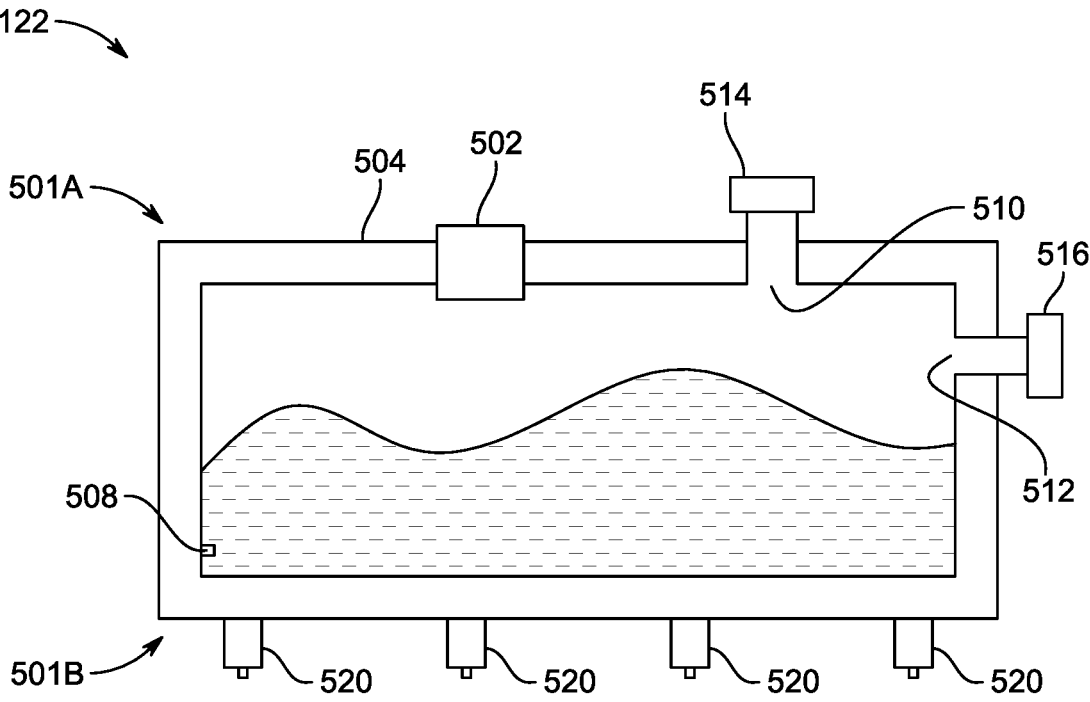
FIG. 5 is a schematic diagram of a fluid chamber of the heart support apparatus of FIG. 1B, according to certain embodiments.

Referring to FIG. 5, a schematic diagram of the fluid chamber 122 of the external device 104 is illustrated, according to an embodiment of the present disclosure. The fluid chamber 122 of the external device 104 may be a storage container having a volume for storing the one or more fluids. In some embodiments, the fluid chamber 122 of the external device 104 is configured to heat the one or more fluids through a dry heating element 502. The dry heating element 502 is connected to the fluid chamber 122. In particular, the dry heating element 502 may be connected to a wall 504 of the fluid chamber 122. The dry heating element 502 is responsible for heating the one or more fluids to a desired temperature within a safe and physiological range. In addition, to maintain the temperature within the safe and physiological range, the fluid chamber 122 of the external device 104 has a temperature control system with a temperature sensor 508. In other words, the temperature sensor 508 is configured to be thermally coupled with the fluid chamber 122 and in direct contact with the one or more fluids in order to sense the temperature of the one or more fluids present in the fluid chamber 122. In some embodiments, the temperature sensor 508 may be in electric communication with the controller 140, as such, the controller 140 and the temperature sensor 508 may together constitute the temperature control system. The temperature sensor 508 may generate a signal indicative of a temperature of the one or more fluids and communicated the signals with the controller 140. The controller 140 may further determine the temperature of the one or more fluids based on the signals received from the temperature sensor 508. In some embodiments, the fluid chamber 122 may be formed of heat-tolerating materials and have airtight and heat resistant seals, in order to prevent any leaks during its operation. The fluid chamber 122 may be manufactured using materials including, but not limited to, inert metals, metal-alloys, high temperature PVC, stainless steel, and heat resistant plastic materials.

The fluid chamber 122 of the external device 104 further includes an upstream inlet 510 to fill the fluid chamber 122 with the one or more fluids and a downstream outlet 512 to withdraw the one or more fluids from the fluid chamber 122. The upstream inlet 510 and the downstream outlet 512 may be defined in the wall 504 of the fluid chamber 122. The upstream inlet 510 may be defined in the wall 504 at a top end 501A of the fluid chamber 122 and the downstream outlet 512 may be defined in the wall 504 at a side of the fluid chamber 122 near the top end 501A of the fluid chamber 122. In some embodiments, the upstream inlet 510 may be configured with a first inlet valve 514 and the downstream outlet 512 may be configured with a second inlet valve 516. The first inlet valve 514 may be controlled to fill the fluid chamber 122 with the one or more fluid whereas the second inlet valve 516 may be controlled to return excessive fluid, or withdraw the one or more fluids, to a main chamber after each cycle of operation of the heart support apparatus 100. In some embodiments, the first inlet valve 514 and the second inlet valve 516 may be electronically actuated valves. In such a case, the first inlet valve 514 and the second inlet valve 516 may electrically communicate with the controller 140 such that the actuation of the first inlet valve 514 and the second inlet valve 516 may be controlled by the controller 140 in response to certain input parameters preset in the controller 140 or provided by the user.

The four piston pumps 120 are disposed at the top end 501A of the fluid chamber 122 and a plurality of outlet valves 520 are disposed at a lower end 501B of the fluid chamber 122. In particular, the fluid chamber 122 includes four outlet valves 520 coupled to the lower end 501B of the fluid chamber 122. Furthermore, the four outlet valves 520 are connected to the fluid tube 114. In some embodiments, the four outlet valves 520 may be electronically actuated valves. In such a case, the four outlet valves 520 may electrically communicate with the controller 140 such that the actuation of the four outlet valves 520 may be controlled by the controller 140 in response to certain input parameters preset in the controller 140. As such, the four outlet valves 520 may further regulate a quantity and flow rate of the one or more fluids transmitting through the fluid tube 114 to the four inflatable compartments 202 of the heart wrap 102. Furthermore, the four piston pumps 120 are coupled with the check valves 401 to block backflow of the one or more fluids from the four outlet valves 520.

As shown in FIG. 1B, the external device 104 of the heart support apparatus 100 includes the pressure relief valve 150 configured to control an amount of the one or more fluids pumped into the heart wrap 102. The pressure relief valve 150 is also configured to prevent extra pressure from building up in the heart support apparatus 100. Furthermore, to complement the pressure relief valve 150, the external device 104 includes the reservoir 152 to receive excessive amount of the one or more fluids from the pressure relief valve 150. In other words, the reservoir 152 is configured to function as an external storage container and contain excess amounts of the one or more fluids, used in the heart support apparatus 100. Moreover, the external device 104 is coupled to the plurality of pressure sensors 154 and the plurality of flow sensors 156. In an embodiment, the plurality of pressure sensors 154 may be coupled with the pressure relief valve 150 or the fluid tube 114 in order to determine an excess pressure built up in the heart support apparatus 100. In a similar manner, the plurality of flow sensors 156 determines the flow rate of the one or more fluids flowing through the fluid tube 114 of the heart support apparatus 100 to further enable an operator to precisely control the amount of the one or more fluids being pumped into the four inflatable compartments 202 of the heart wrap 102 included in the heart support apparatus 100. In an embodiment, the pressure sensors 154 and the flow sensors 156 may be in electric communication with the controller 140. The pressure sensors 154 and the flow sensors 156 may generate signals indicative of a pressure and flow rate, respectively, of the one or more fluids flowing through the fluid tube 114 and communicate the signals with the controller 140. The controller 140 may further determine the pressure and the flow rate of the one or more fluids based on the signals received from the pressure sensor 154 and the flow sensors 156, respectively.

Figure 6:
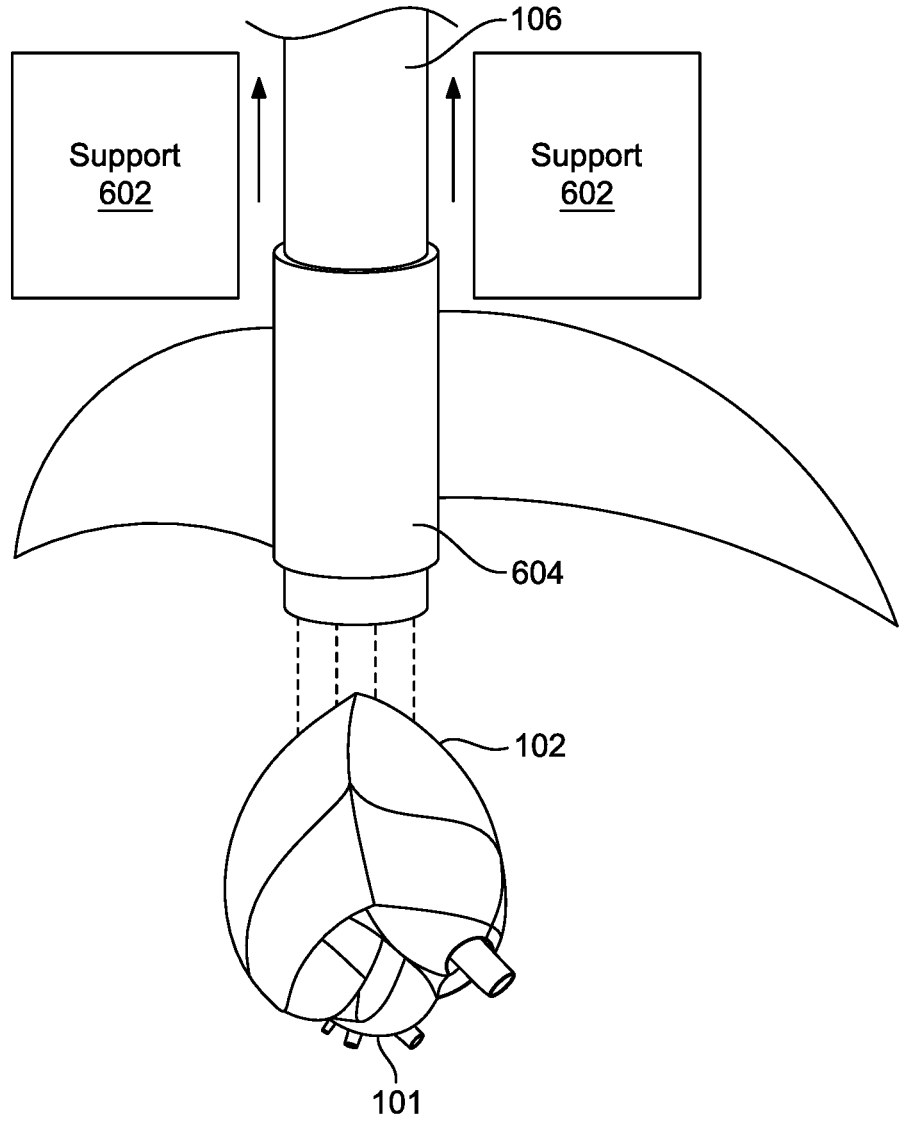
FIG. 6 is a schematic block diagram of a support of the heart support apparatus, according to certain embodiments.

Referring to FIG. 6, a schematic diagram of a support 602 for holding the connector tube 106 in the chest cavity of the patient is illustrated, according to certain embodiments. The support 602 helps to hold an external tube 604 for insertion of the connector tube 106 into the chest cavity of the patient. In some embodiments, the external tube 604 is configured to have larger diameter than a diameter of the connector tube 106. In some embodiments, during the insertion of the heart wrap 102 and associated components, the support 602 may be inserted near the chest cavity of the patient. As such, the support 602 may be configured to hold the external tube 604, securely in place, which makes a safe passage for the connector tube 106 and the heart wrap 102. The support 602 may be held between the muscular tissue of the patient. Further, the support 602 holds the connector tube 106 in order to maintain a sterile and solid connection between the connector tube 106 and the heart wrap 102. The external tube 604, held by the support 602, may make it easy for the connector tube 106 and the heart wrap 102 to be pulled out, when the patient sufficiently recovers post using the heart support apparatus 100.

The heart support apparatus 100 of the present disclosure may be used in patients post an open-heart surgery. In a first scenario, after an open-heart surgery, the cardiologist may apply the heart wrap 102 of the heart support apparatus 100 to support the heart as needed. The heart wrap may be applied to the heart prior to closing the chest following the open-heart surgery. In a second scenario, the patient is transferred to the cardiac critical care unit for closed monitoring while being intubated and anesthetized. During this period, a suction tube is usually applied for pericardial drainage, helping remove excess blood or fluids following the surgery. Herein, the heart support apparatus 100 including the external device 104, the first suction tube 116 and the second suction tube 118 may be utilized. Additionally, the heart support apparatus 100 of the present disclosure may also be used in adult patients with heart ailments such as heart failure, or hear attack. During an insertion stage of a procedure of placement of the heart wrap 102, the patient is prepared, and all medical personnel and equipment are arranged in place. During such a procedure, sterile conditions are maintained throughout the procedure. Initially, the patient is generally administered general anesthesia or local anesthesia to ensure that the patient is unconscious or pain-free during the procedure. Further, a small incision is made in the chest, similar to the location used for cardiac tamponade needle decompression. The incision provides access to the pericardial space around the heart. Further, using specialized instruments such as a scope, a surgeon may carefully explore the pericardial space to ensure that there are no adhesions or anomalies that could interfere with the placement of the heart wrap 102. Then, the heart wrap 102 of the heart support apparatus 100, comprising of a flexible and biocompatible material, is inserted through the incision. It is positioned around the heart 101 of the patient in such a way that allows the heart wrap 102 to provide gentle external support and rhythmic compressions. The support 602 of the heart support apparatus is used to position the heart wrap 102 around the heart 101 of the patient.

Upon insertion of the heart wrap 102, the heart wrap 102 is carefully ensured in place. The positioning and tension of the heart wrap 102 are adjusted to provide support without causing excessive compression. Once the heart wrap 102 is securely positioned in place, the connector tube 106 housing the negative lead cable 108, the positive lead cable 110, the first suction tube 116, the second suction tube 118, and the fluid tube 114 is connected to the heart wrap 102. The fluid tube 114 is further coupled with the external device 104 including the piston pumps 120 and the fluid chamber 122. The first suction tube 116 and the second suction tube 118 are fluidly connected to the vessel 130. The positive lead cable 110 and the negative lead cable 108 are electrically coupled to the power source 112. These external systems including the piston pumps 120, the fluid chamber 122, the power source 112, the controller 140, the vessel 130, the pressure relief valve 150, the plurality of flow sensors 156, the plurality of pressure sensors 154, and the connector tube 106 allow controlled inflation and deflation of the inflatable compartments 202 of the heart wrap 102, thereby replicating the heart's pumping action. Finally, the heart support apparatus 100 is tested and calibrated to ensure proper functioning of and synchronization with the patient's cardiovascular system.

Once the patient's heart function is stabilized or improved, and the need for external assistance is diminished, the heart wrap 102 is removed, at removal stage. The patient is taken to the operating room under sterile conditions. Anesthesia is administered as needed. The original incision made for the insertion of the heart wrap 102 is carefully reopened. The inflatable compartments 202 of the heart wrap 102 are gradually deflated to relieve any compression on the heart 101. The connector tube 106 connecting the heart wrap 102 to the external systems is disconnected. Sutures or clips securing the heart wrap 102 are carefully removed. Further, the heart wrap 102 is gently extracted from around the heart 101. Care is taken to avoid any trauma to the heart 101 or surrounding tissues and then, the incision is closed using appropriate sutures or wound closure techniques. The patient is closely monitored during the recovery period.

Figure 7:
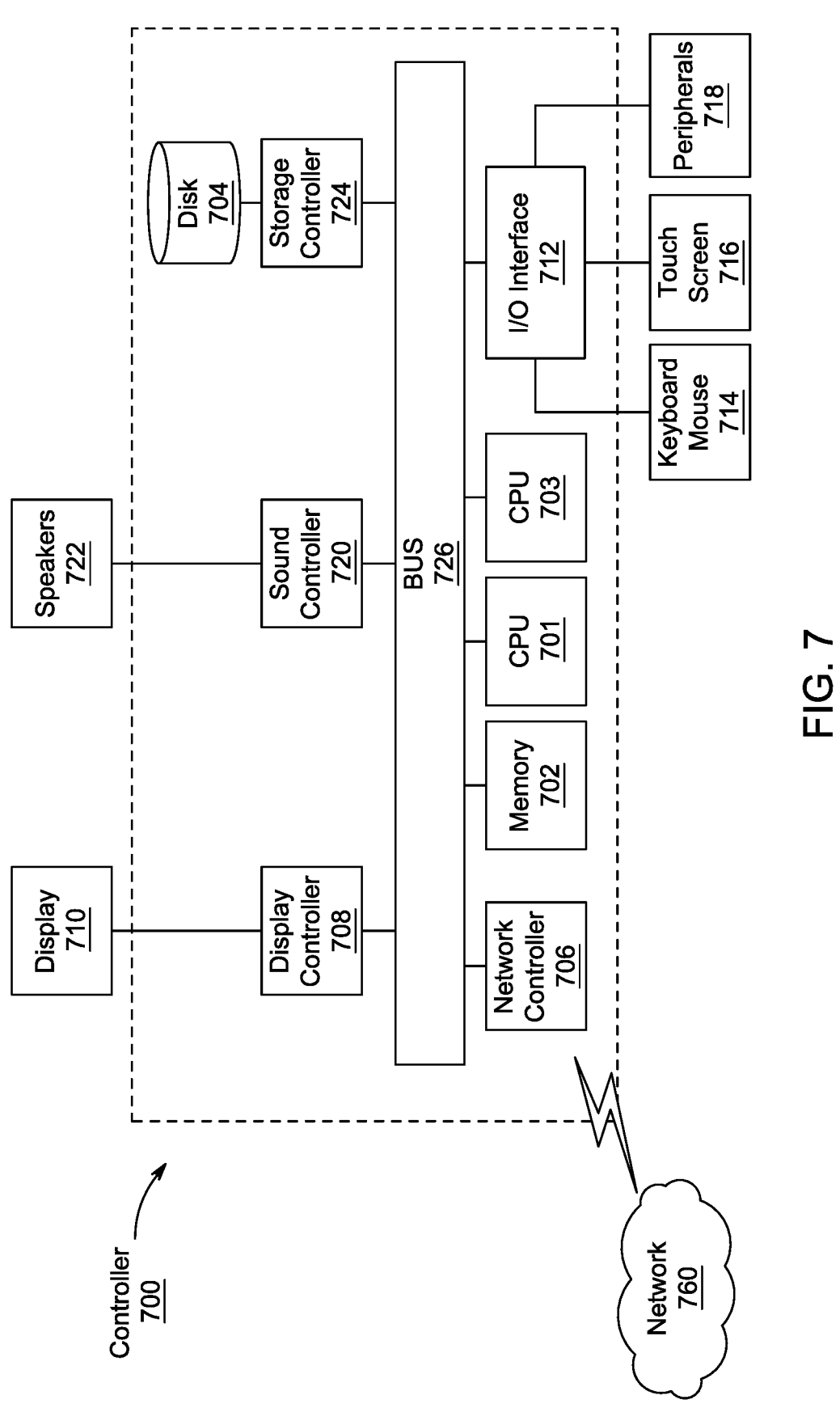
FIG. 7 is an illustration of a non-limiting example of details of computing hardware used in a computing system, according to certain embodiments.

Referring to FIG. 7, a block diagram of a non-limiting example of computer hardware used in a computing system is illustrated, according to certain embodiments. The computing system, in the present disclosure, may refer to the controller 140 and supporting components. The controller 140 allows medical professional to adjust a plurality of parameters of the heart support apparatus 100. Further, the controller 140 maintains authentication protocols in order to prevent unauthorized access to the heart support apparatus 100.

In FIG. 7, a controller 700 is described which is representative of the controller 140 of FIG. 1B in which the controller is a computing device which includes a CPU 701 which performs the processes described above/below. The process data and instructions may be stored in memory 702. These processes and instructions may also be stored on a storage medium disk 704 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 701, 703 and an operating system such as Microsoft Windows 7, Microsoft Windows 10, Microsoft Windows 11, UNIX, Solaris, LINUX, Apple MAC-OS, and other systems known to those skilled in the art.

The hardware elements in order to achieve the computing device may be realized by various circuitry elements, known to those skilled in the art. For example, CPU 701 or CPU 703 may be a Xenon or Core processor from Intel of America or an Opteron processor from AMD of America, or may be other processor types that would be recognized by one of ordinary skill in the art. Alternatively, the CPU 701, 703 may be implemented on an FPGA, ASIC, PLD or using discrete logic circuits, as one of ordinary skill in the art would recognize. Further, CPU 701, 703 may be implemented as multiple processors cooperatively working in parallel to perform the instructions of the inventive processes described above.

The computing device in FIG. 7 also includes a network controller 706, such as an Intel Ethernet PRO network interface card from Intel Corporation of America, for interfacing with network 760. As can be appreciated, the network 760 can be a public network, such as the Internet, or a private network such as an LAN or WAN network, or any combination thereof and can also include PSTN or ISDN subnetworks. The network 760 can also be wired, such as an Ethernet network, or can be wireless such as a cellular network including EDGE, 3G, 4G and 5G wireless cellular systems. The wireless network can also be Wi-Fi, Bluetooth, or any other wireless form of communication that is known.

The computing device further includes a display controller 708, such as a NVIDIA GeForce GTX or Quadro graphics adaptor from NVIDIA Corporation of America for interfacing with display 710, such as a Hewlett Packard HPL2445w LCD monitor. A general purpose I/O interface 712 interfaces with a keyboard and/or mouse 714 as well as a touch screen panel 716 on or separate from display 710. General purpose I/O interface also connects to a variety of peripherals 718 including printers and scanners, such as an OfficeJet or DeskJet from Hewlett Packard.

A sound controller 720 is also provided in the computing device such as Sound Blaster X-Fi Titanium from Creative, to interface with speakers/microphone 722 thereby providing sounds and/or music.

The general-purpose storage controller 724 connects the storage medium disk 704 with communication bus 726, which may be an ISA, EISA, VESA, PCI, or similar, for interconnecting all of the components of the computing device. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 8.

Figure 8:
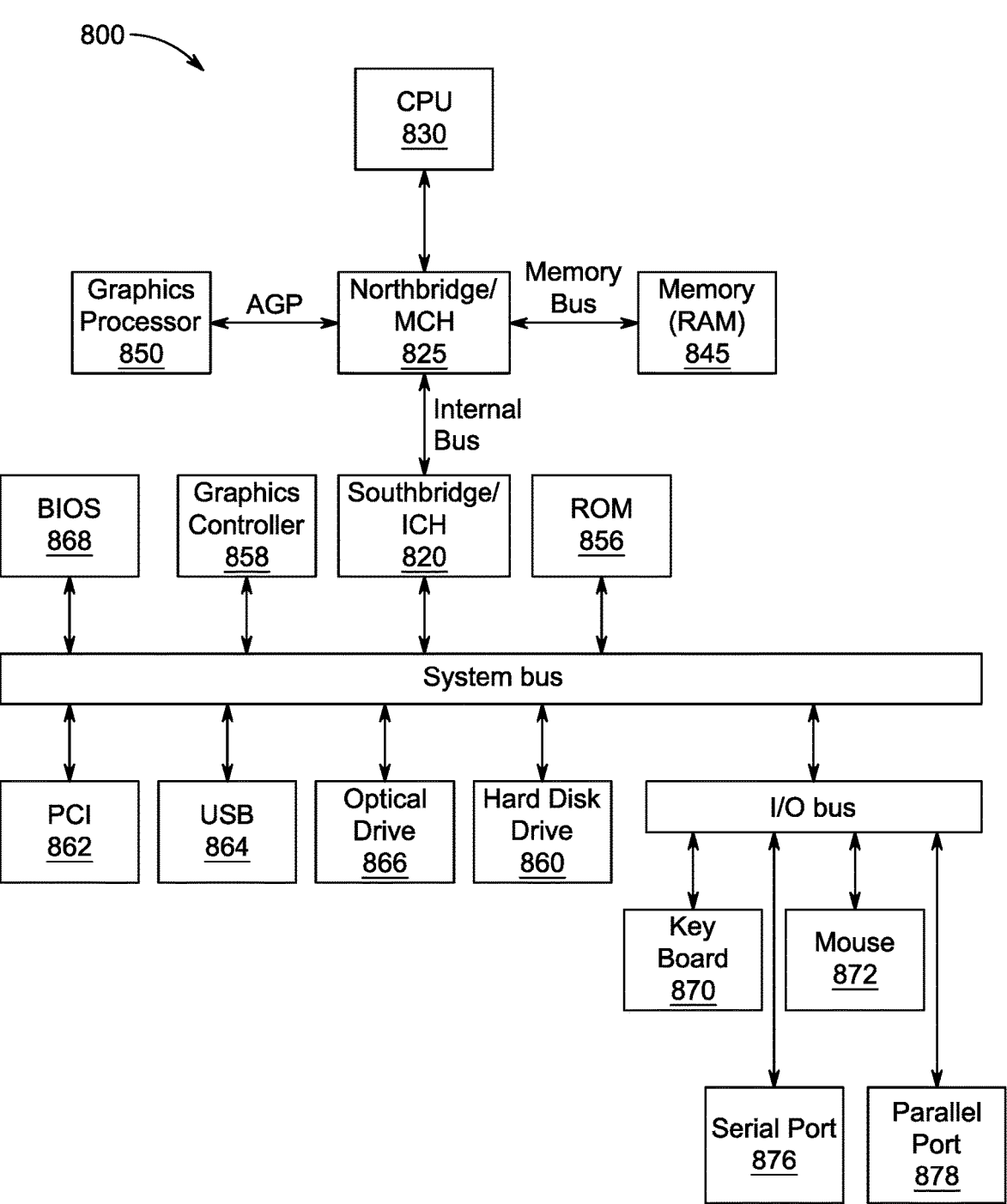
FIG. 8 is an exemplary schematic diagram of a data processing system used within the computing system, according to certain embodiments.

Referring to FIG. 8, a schematic diagram of a data processing system, according to certain embodiments, for performing the functions of the exemplary embodiments. The data processing system is an example of a computer in which code or instructions implementing the processes of the illustrative embodiments may be located.

In FIG. 8, data processing system 800 employs a hub architecture including a north bridge and memory controller hub (NB/MCH) 825 and a south bridge and input/output (I/O) controller hub (SB/ICH) 820. The central processing unit (CPU) 830 is connected to NB/MCH 825. The NB/MCH 825 also connects to the memory 845 via a memory bus and connects to the graphics processor 850 via an accelerated graphics port (AGP). The NB/MCH 825 also connects to the SB/ICH 820 via an internal bus (e.g., a unified media interface or a direct media interface). The CPU Processing unit 830 may contain one or more processors and even may be implemented using one or more heterogeneous processor systems.

Figure 9:
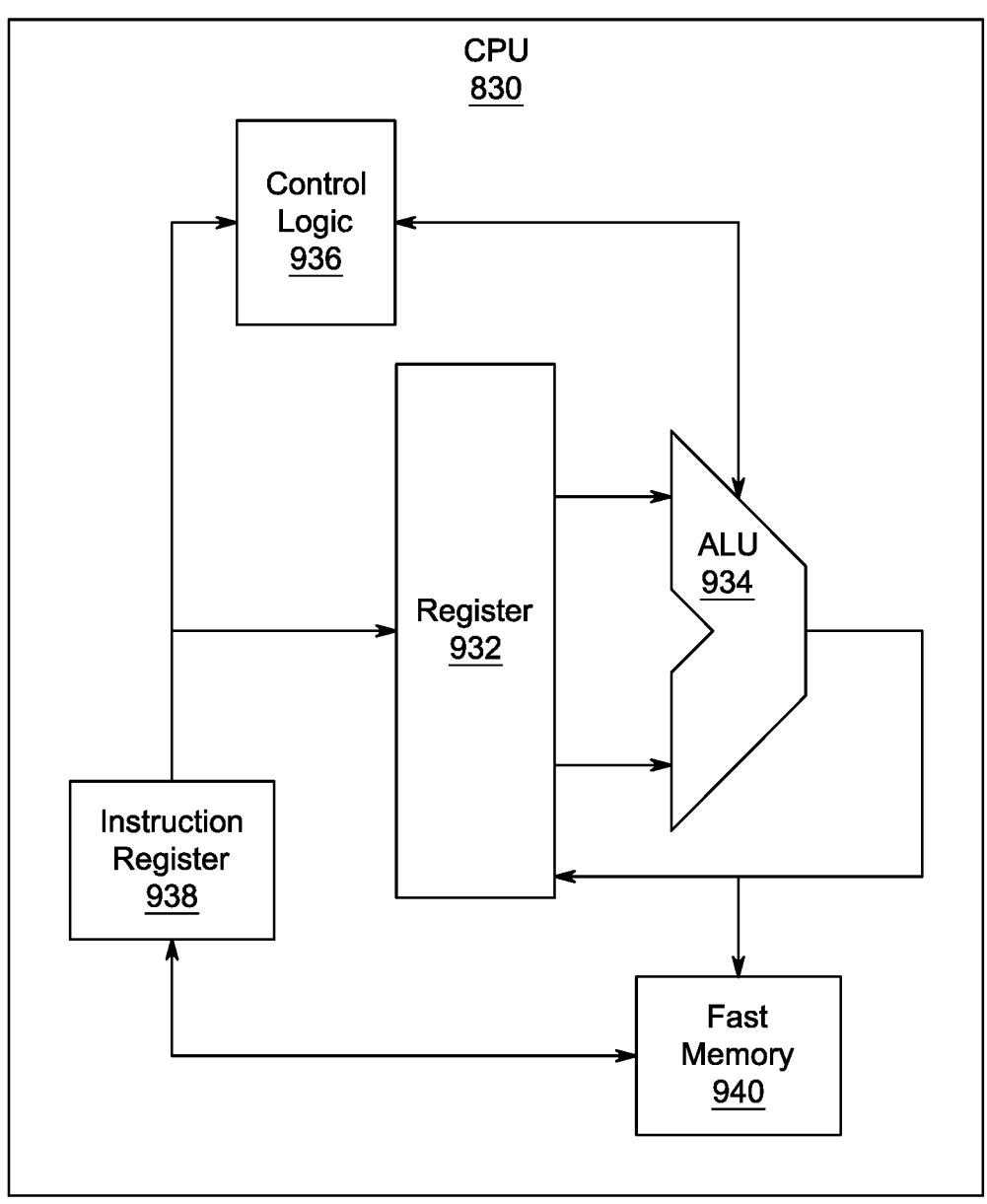
FIG. 9 is an exemplary schematic diagram of a processor used with the computing system, according to certain embodiments.

For example, FIG. 9 shows one implementation of CPU 830. In one implementation, the instruction register 938 retrieves instructions from the fast memory 940. At least part of these instructions are fetched from the instruction register 938 by the control logic 936 and interpreted according to the instruction set architecture of the CPU 830. Part of the instructions can also be directed to the register 932. In one implementation the instructions are decoded according to a hardwired method, and in another implementation the instructions are decoded according to a microprogram that translates instructions into sets of CPU configuration signals that are applied sequentially over multiple clock pulses. After fetching and decoding the instructions, the instructions are executed using the arithmetic logic unit (ALU) 934 that loads values from the register 932 and performs logical and mathematical operations on the loaded values according to the instructions. The results from these operations can be feedback into the register and/or stored in the fast memory 940. According to certain implementations, the instruction set architecture of the CPU 830 can use a reduced instruction set architecture, a complex instruction set architecture, a vector processor architecture, a very large instruction word architecture. Furthermore, the CPU 830 can be based on the Von Neuman model or the Harvard model. The CPU 830 can be a digital signal processor, an FPGA, an ASIC, a PLA, a PLD, or a CPLD. Further, the CPU 830 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 8, the data processing system 800 can include that the SB/ICH 820 is coupled through a system bus to an I/O Bus, a read only memory (ROM) 856, universal serial bus (USB) port 864, a flash binary input/output system (BIOS) 868, and a graphics controller 858. PCI/PCIe devices can also be coupled to SB/ICH 888 through a PCI bus 862.

The PCI devices may include, for example, Ethernet adapters, add-in cards, and PC cards for notebook computers. The Hard disk drive 860 and CD-ROM 866 can use, for example, an integrated drive electronics (IDE) or serial advanced technology attachment (SATA) interface. In one implementation the I/O bus can include a super I/O (SIO) device.

Further, the hard disk drive (HDD) 860 and optical drive 866 can also be coupled to the SB/ICH 820 through a system bus. In one implementation, a keyboard 870, a mouse 872, a parallel port 878, and a serial port 876 can be connected to the system bus through the I/O bus. Other peripherals and devices that can be connected to the SB/ICH 820 using a mass storage controller such as SATA or PATA, an Ethernet port, an ISA bus, a LPC bridge, SM-Bus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

While aspects of the present disclosure have been particularly shown and described with reference to the embodiments above, it will be understood by those skilled in the art that various additional embodiments may be contemplated by the modification of the disclosed methods and systems without departing from the spirit and scope of what is disclosed. Such embodiments should be understood to fall within the scope of the present disclosure as determined based upon the claims and any equivalents thereof.

The invention claimed is:

1. A heart support apparatus for massaging a heart of a patient, comprising:

a heart wrap having a shape configured to conform with the heart of the patient, wherein the heart wrap is divided in four inflatable compartments such that each inflatable compartment of the four inflatable compartments is configured to completely cover one of a right atrium, a left atrium, a right ventricle, or a left ventricle of the heart, respectively;

a negative charge pad placed inside a first inflatable compartment of the four inflatable compartments that covers the right atrium of the heart configured to deliver an electrical stimulus to the heart of the patient, wherein the negative charge pad is connected to a power source through a negative lead cable;

a positive charge pad placed inside a second inflatable compartment of the four inflatable compartments that covers the left ventricle of the heart configured to receive the electrical stimulus, wherein the positive charge pad is connected to the power source through a positive lead cable;

an external device with four piston pumps and a fluid chamber configured to circulate one or more fluids to the four inflatable compartments of the heart wrap through a fluid tube;

a first suction tube configured to remove a first fluid from an internal space between an outer surface of the human heart and an inner surface of the heart wrap;

a second suction tube configured to remove a second fluid from an outer space between an outer surface of the heart wrap and a chest cavity of the patient;

a connector tube configured to connect the external device to the heart wrap, wherein the connector tube includes the negative lead cable, the positive lead cable, the fluid tube, the first suction tube, and the second suction tube;

wherein the first suction tube and the second suction tube are connected to a vessel in the external device to receive the first fluid and the second fluid; and a controller with program instructions configured to control a set of parameters of the four piston pumps.

2. The heart support apparatus of claim 1, wherein the four piston pumps are integrated with a pair of peristaltic pumps.

3. The heart support apparatus of claim 2, wherein a first peristaltic pump of the pair of peristaltic pumps is connected to two inflatable compartments of the four inflatable compartments of the heart wrap that cover the right atrium and the right ventricle.

4. The heart support apparatus of claim 2, wherein a second peristaltic pump of the pair of peristaltic pumps is connected to two inflatable compartments of the four inflatable compartments of the heart wrap that cover the left atrium and the left ventricle.

5. The heart support apparatus of claim 1, wherein the fluid chamber of the external device is configured to heat the one or more fluids through a dry heating element connected to the fluid chamber.

6. The heart support apparatus of claim 1, wherein the fluid chamber of the external device has a temperature control system with a temperature sensor.

7. The heart support apparatus of claim 1, wherein the fluid chamber of the external device includes an upstream inlet to fill the fluid chamber with the one or more fluids and a downstream outlet to withdraw the one or more fluids from the fluid chamber.

8. The heart support apparatus of claim 1, further comprising a support to hold the connector tube for insertion of the connector tube into the chest cavity of the patient.

9. The heart support apparatus of claim 1, wherein the four piston pumps are at a top end of the fluid chamber and four outlet valves at a lower end.

10. The heart support apparatus of claim 9, wherein the four outlet valves are connected to the fluid tube.

11. The heart support apparatus of claim 1, wherein an inner surface of the four inflatable compartments of the heart wrap is a porous foam.

12. The heart support apparatus of claim 1, wherein each inflatable compartment is formed of a foamed polymer, wherein an inner portion of each inflatable compartment has an open cell structure, and an outer surface portion of each inflatable compartment has an impermeable skin, wherein both the inner portion and the outer skin portion consist of the same polymer.

13. The heart support apparatus of claim 1, wherein the heart wrap is made of a material selected from a silicon polymer and a poly vinyl chloride (PVC).

14. The heart support apparatus of claim 1, wherein the power source connected to the positive charge pad and the negative charge pad is coupled to the external device, wherein at least a major portion of the negative charge pad is embedded with one of the inflatable compartments.

15. The heart support apparatus of claim 1, wherein each of the four piston pumps is coupled to a check valve resulting in four check valves configured to block backflow of the one or more fluids from the four outlet valves.

16. The heart support apparatus of claim 1, wherein the external device includes a pressure relief valve configured to control an amount of the one or more fluids pumped into the heart wrap.

17. The heart support apparatus of claim 16, wherein the external device includes a reservoir to receive excessive amount of the one or more fluids from the pressure relief valve.

18. The heart support apparatus of claim 1, wherein the external device is coupled to a plurality of pressure sensors and a plurality of flow sensors.

19. The heart support apparatus of claim 1, wherein the heart wrap has a cone shape.

20. The heart support apparatus of claim 1, wherein the controller is an electronic controller with a user-interface.

\* \* \* \* \*